(12) United States Patent
Cooper et al.

(10) Patent No.: US 9,709,787 B2
(45) Date of Patent: Jul. 18, 2017

(54) MICROSCOPY INSTRUMENTS WITH BEAM SPLITTING SYSTEM INCLUDING OPTICAL FILTERS AND MIRRORS

(75) Inventors: Jeremy R. Cooper, Issaquah, WA (US); Justin Kyle Curts, Issaquah, WA (US)

(73) Assignee: GE Healthcare Bio-Sciences Corp., Piscataway, NJ (US)

( * ) Notice: Subject to any disclaimer, the term of this patent is extended or adjusted under 35 U.S.C. 154(b) by 127 days.

(21) Appl. No.: 14/234,425

(22) PCT Filed: Jul. 10, 2012

(86) PCT No.: PCT/SE2012/050820
§ 371 (c)(1),
(2), (4) Date: Jan. 23, 2014

(87) PCT Pub. No.: WO2013/015733
PCT Pub. Date: Jan. 31, 2013

(65) Prior Publication Data
US 2014/0158865 A1 Jun. 12, 2014

Related U.S. Application Data

(60) Provisional application No. 61/511,093, filed on Jul. 24, 2011.

(51) Int. Cl.
*G02B 21/06* (2006.01)
*G01N 21/64* (2006.01)
*G02B 21/16* (2006.01)

(52) U.S. Cl.
CPC ......... *G02B 21/06* (2013.01); *G01N 21/6458* (2013.01); *G02B 21/16* (2013.01);
(Continued)

(58) Field of Classification Search
CPC .......... G02B 5/20; G02B 5/201; G02B 5/204; G02B 5/205; G02B 5/206; G02B 5/26;
(Continued)

(56) References Cited

U.S. PATENT DOCUMENTS 4,786,813 A * 11/1988 Svanberg ............... G01J 3/02
250/458.1
5,689,334 A 11/1997 Atkinson et al.
(Continued)

FOREIGN PATENT DOCUMENTS

EP   1 403 675 A2   3/2004
EP   1 441 219 A2   7/2004
(Continued)

OTHER PUBLICATIONS

EP Search Report for EP Application No. 128 17 277 mailed Feb. 9, 2015 (3 pages).
(Continued)

*Primary Examiner* — Seung C Sohn
(74) *Attorney, Agent, or Firm* — Eversheds Sutherland (US) LLP

(57) ABSTRACT

Microscopy instruments with detectors located on one side of the instruments are disclosed. The microscopy instruments include a splitting system and an array of detectors disposed on one side of the instrument. A beam composed of two or more separate emission channels is separated by the splitting system into two or more beams that travel along separate paths so that each beam reaches a different detector in the array of detectors. Each beam is a different emission channel and the beams are substantially parallel.

19 Claims, 10 Drawing Sheets

(52) U.S. Cl.
CPC ........... *G01N 2021/6419* (2013.01); *G01N 2021/6421* (2013.01); *G01N 2021/6423* (2013.01)

(58) Field of Classification Search
CPC ........ G02B 5/265; G02B 21/06; G02B 21/16; G01N 21/6458; G01N 2021/6419; G01N 2021/6421; G01N 2021/6423
USPC ......... 250/226, 216, 208.1, 306, 307, 336.1, 250/361 R, 362, 363.01, 363.02, 370.08, 250/372, 458.1, 459.1, 462.1, 472.1, 250/473.1, 483.1, 203.3; 359/368, 372; 356/337, 338
See application file for complete search history.

(56) References Cited

U.S. PATENT DOCUMENTS

| | | | |
|---|---|---|---|
| 5,982,497 A | 11/1999 | Hopkins | |
| 7,005,645 B2* | 2/2006 | Von Drasek | F23N 5/00 250/339.13 |
| 7,190,514 B2* | 3/2007 | Mikuriya et al. | 359/385 |
| 7,468,796 B2* | 12/2008 | Luther | G01N 15/1468 356/411 |
| 7,697,975 B2 | 4/2010 | Zeng | |
| 9,547,178 B2* | 1/2017 | Erdogan | G02B 5/26 |
| 2011/0043907 A1 | 2/2011 | Sasai | |
| 2011/0096393 A1 | 4/2011 | Araki | |
| 2013/0155218 A1 | 6/2013 | Kalkbrenner et al. | |

FOREIGN PATENT DOCUMENTS

| | | |
|---|---|---|
| EP | 1 688 734 A1 | 8/2006 |
| EP | 2146234 A1 | 1/2010 |
| JP | S62-238427 A | 10/1987 |
| JP | 4-104243 | 4/1992 |
| JP | H11-275429 A | 10/1999 |
| WO | WO 2010/084478 | 7/2010 |
| WO | WO 2011/085765 | 7/2011 |

OTHER PUBLICATIONS

Japanese Office Action for JP Applciation No. 2014-522789 mailed May 10, 2016 (3 pages).

* cited by examiner

MICROSCOPY INSTRUMENTS WITH BEAM SPLITTING SYSTEM INCLUDING OPTICAL FILTERS AND MIRRORS

CROSS-REFERENCE TO A RELATED APPLICATION

This application is a filing under 35 U.S.C. 371 of international application number PCT/SE2012/050820, filed Jul. 10, 2012, published on Jan. 31, 2013 as WO 2013/015733, which claims the benefit of Provisional Application No. 61/511,093; filed Jul. 24, 2011.

TECHNICAL FIELD

This disclosure relates to fluorescence microscopy and, in particular, to fluorescence microscopy instruments with camera systems.

BACKGROUND

Multi-camera fluorescence microscopy provides a dedicated camera for each fluorescent emission channel allowing for improved speed and optical optimization. However, splitting the fluorescent emission channels into different optical paths and directing each emission channel to a separate camera often results in asymmetric and complicated optical systems. Consider for example a typical microscope with three cameras located on three different sides of the microscope. Light composed of three emission channels emitted from three different fluorescently labeled components of a specimen is collected by an objective lens. The light exits the objective lens and is split by the microscope optical system into three separate beams. Each beam is composed of light of one of the emission channels that travels along a separate optical path to one of the three cameras.

However, because the cameras are located on different sides of the microscope, the camera cables and tubes used to transport coolant to the cameras project out of each side of the microscope that includes a camera. As a result, the footprint of the microscope can be large, which may be a problem when attempting to install the microscope in a limited lab space. In addition, the camera layout is asymmetric and irregular cabling and tube projections can substantially diminish the overall aesthetics of the microscope. For these reasons, engineers, scientists, and microscope manufacturers continue to seek microscopes with layouts that reduce the overall footprint of the microscope and are more aesthetically pleasing.

SUMMARY

Microscopy instruments with detectors located on one side of the instruments are disclosed. In one aspect, a microscopy instrument includes a splitting system and an array of detectors disposed on one side of the instrument. A beam composed of two or more separate emission channels travels along an emission path to the splitting system. The splitting system separates the emissions channels so that each emission channel travels along a separate path to one of the detectors in the array of detectors. The two or more paths travelled by the separate emission channels are substantially parallel so that each channel is received by a different detector in the array of detectors.

DETAILED DESCRIPTION

Figure 1:
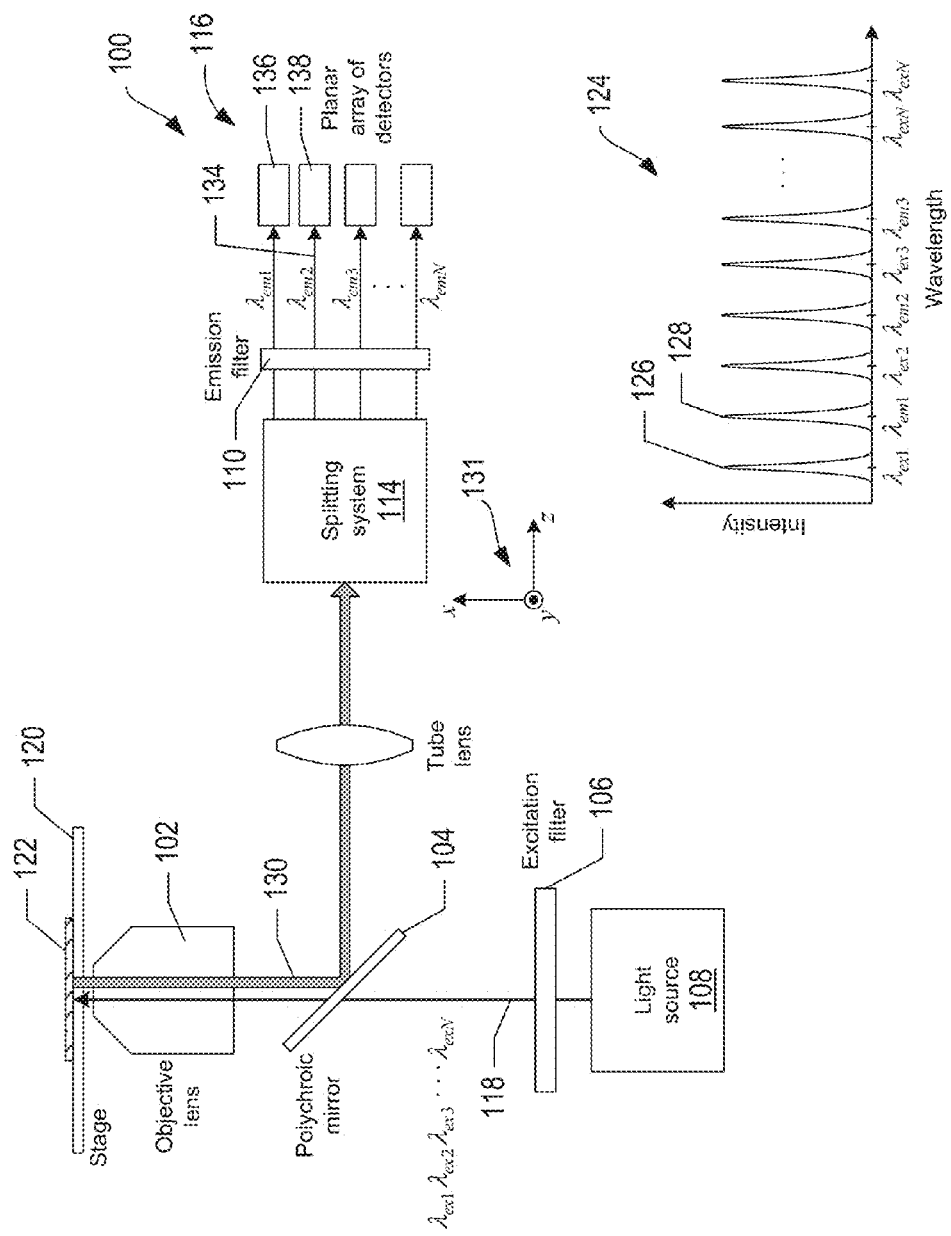
FIG. 1 shows a schematic representation of an example microscopy instrument.

FIG. 1 shows a schematic representation of an example microscopy instrument 100. The instrument 100 includes an objective lens 102, a polychroic mirror 104, an excitation filter 106, a light source 108, an emission filter 110, a tube lens 112, a splitting system 114, and a planar array of detectors 116. The light source 108 can be a laser that emits a high-intensity, substantially monochromatic beam of light 118. The excitation filter 106 and the polychroic mirror 104 transmit the beam of excitation light, which passes through the objective 102 and an aperture in a stage 120 to a specimen disposed on a microscope slide 122 that is supported by the stage 120. The excitation filter 106 prevents out-of-band wavelengths of light from entering the source 108. Components of the specimen are labeled with fluorescent probes. Each type of probe is designed to bind specifically to a particular component of the specimen, and each type of fluorophore is bound to a particular type of probe so that when the specimen is illuminated with the excitation light 118 the different fluorophores emit light with different wavelengths in the visible and near-visible portion of the electromagnetic spectrum. As a result, each component of the specimen is displayed with a different associated wavelength. In the example of FIG. 1, the specimen components are labeled with N different types of fluorophores that each emits light of a different wavelength in the visible spectrum. The wavelengths are denoted by $\lambda_i$, where i is an integer index that ranges from 1 to N. FIG. 1 includes a plot 124 of intensity versus a range of wavelengths in the visible spectrum. Each curve of the plot 124 represents an intensity distribution over a very narrow range of wavelengths centered about a particular wavelength. For example, curve 126 represents a narrow range of excitation wavelengths centered about a wavelength $\lambda_{ex1}$ that produces an emission of light from a first type of fluorophore, and curve 128 represents a narrow range of emission wavelengths centered about a wavelength $\lambda_{em1}$ emitted by the first fluorophore. The N excitation wavelengths denoted by $\lambda_{exi}$, where i is an integer index that ranges from 1 to N, excite emission from the N different types of fluorophores. Each of the N different types of fluorophore emits a corresponding emission wavelength denoted by $\lambda_{emi}$. When the emission wavelengths are in the visible portion of the electromagnetic spectrum, the components appear in an image of the specimen with different colors. The N excitation wavelengths are called "excitation channels," and the N wavelengths of light emitted from the N types of fluorophores are called "emission channels." The N excitation channels $\lambda_{exi}$ comprise the excitation light 118

A portion of the N emission channels are collected and collimated by the objective lens 102 into a single emission beam 130. The beam 130 is reflected from the polychroic mirror 104 to travel along a central optical emission axis that runs parallel to the z-axis of a Cartesian coordinate system 131 associated with the instrument 100. The beam 130 passes through the emission filter 110 which blocks stray excitation light. The tube lens 112 can represent a single lens or represent a number of lenses and other optical elements that focus the beam 130 onto an image plane at the detectors 116 before the beam 130 enters the splitting system 114. In an alternative embodiment, each beam can have its own separate tube lens positioned downstream of the splitting system. The splitting system 114 separates the emission channels of the beam 130 so that each channel follows one of N separate, substantially parallel paths through the emission filter(s) 110 to a detector in the planar array of detectors 116. For example, directional arrows 132 and 134 represent substantially parallel output beams in which the output beam 132 is the emission channels $\lambda_{em1}$ directed to the detector 136 and the output beam 134 is the emission channel $\lambda_{em2}$ directed to the detector 138. Each detector in the array 116 can be a photodetector array, a CCD camera, or a CMOS camera. In an alternative embodiment, each beam can pass through a separate excitation filter. The splitting system 114 and the planar array of detectors 116 form a detection system of the instrument 100. The detectors in the array 116 can have any suitable arrangement but the detectors lie in approximately the same plane facing the splitting system 114.

Figure 2A:
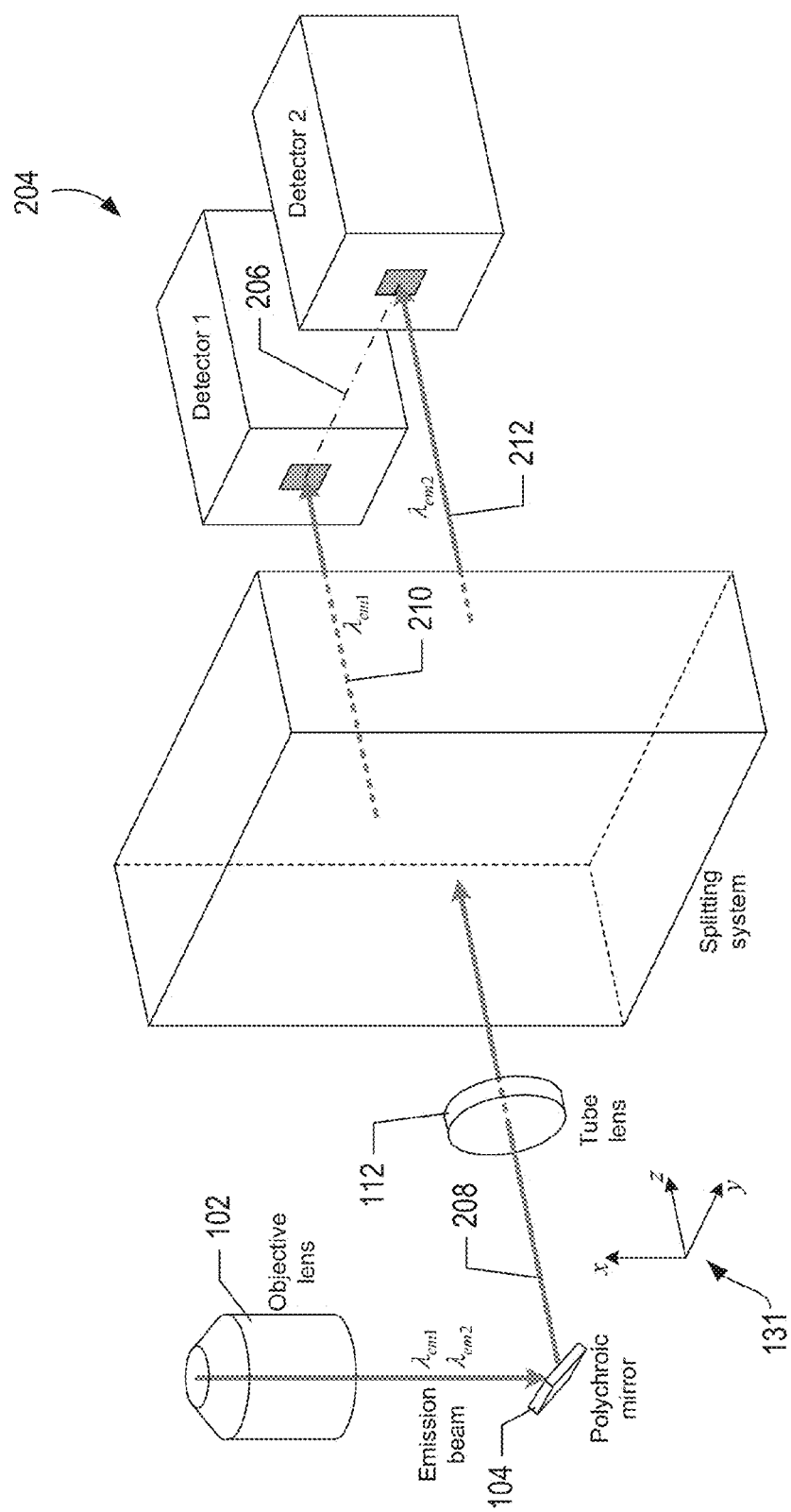
FIGS. 2A-2D show four examples of detection systems associated with four microscopy instruments.
Figure 2B:
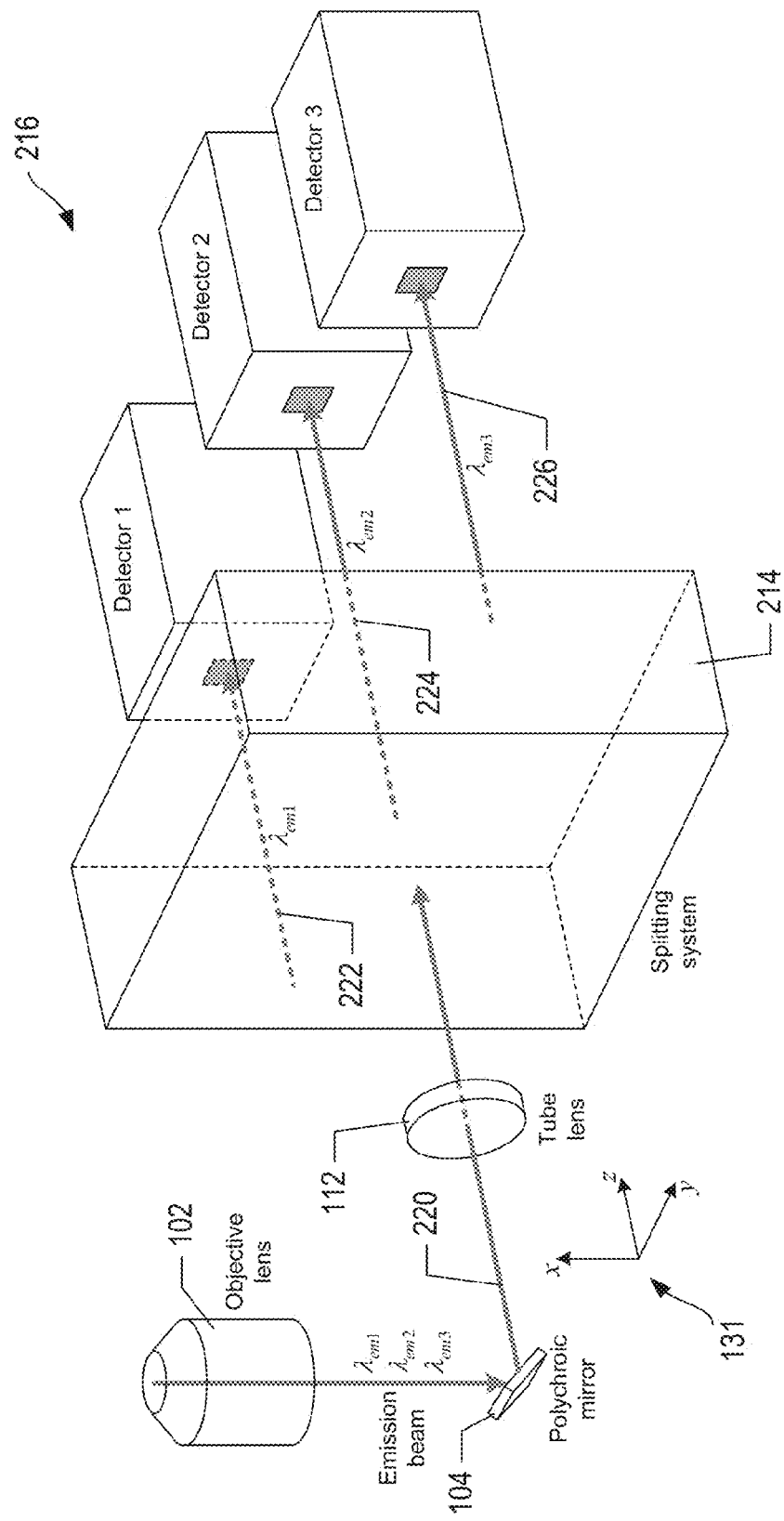
Figure 2C:
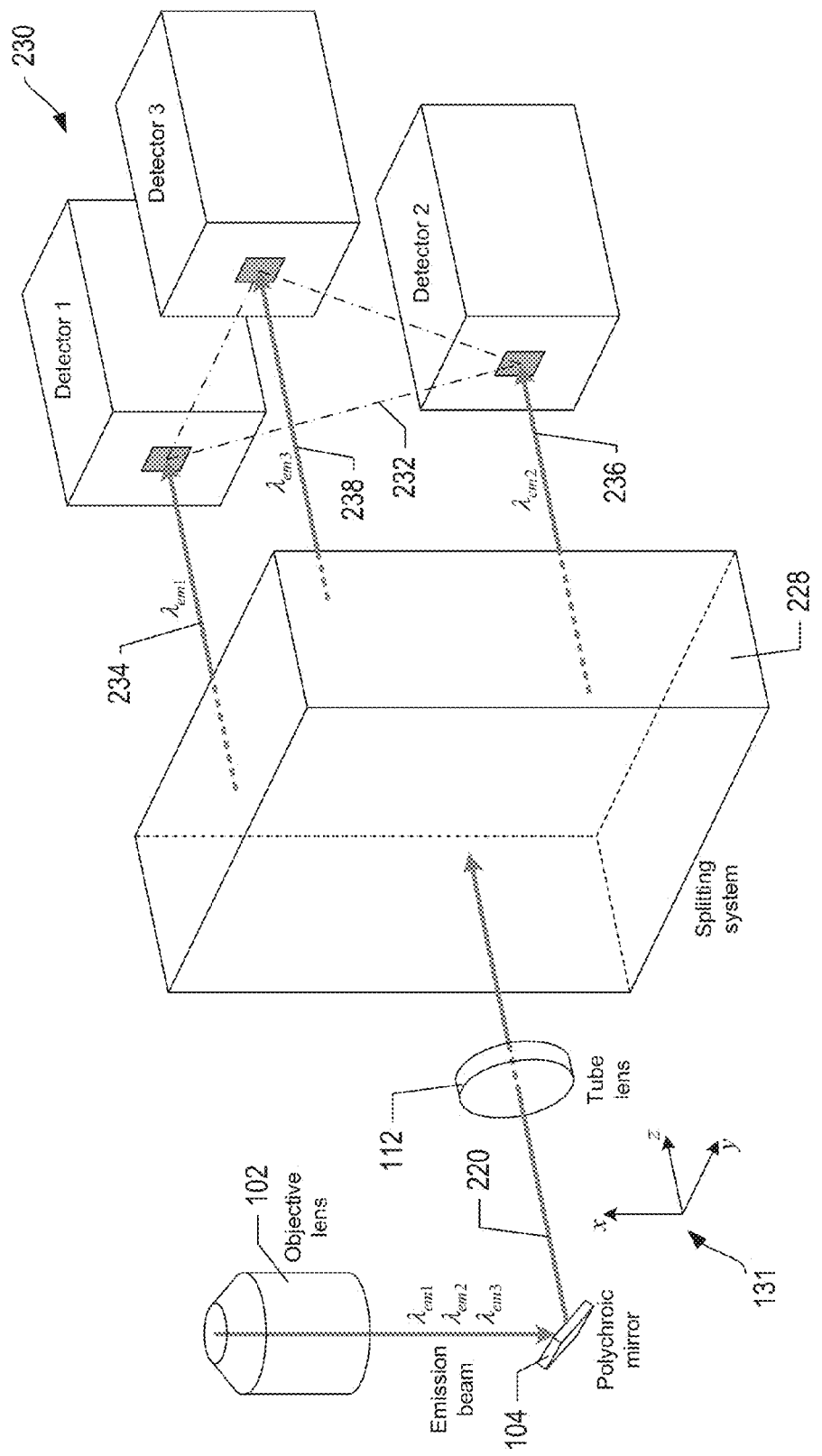
Figure 2D:
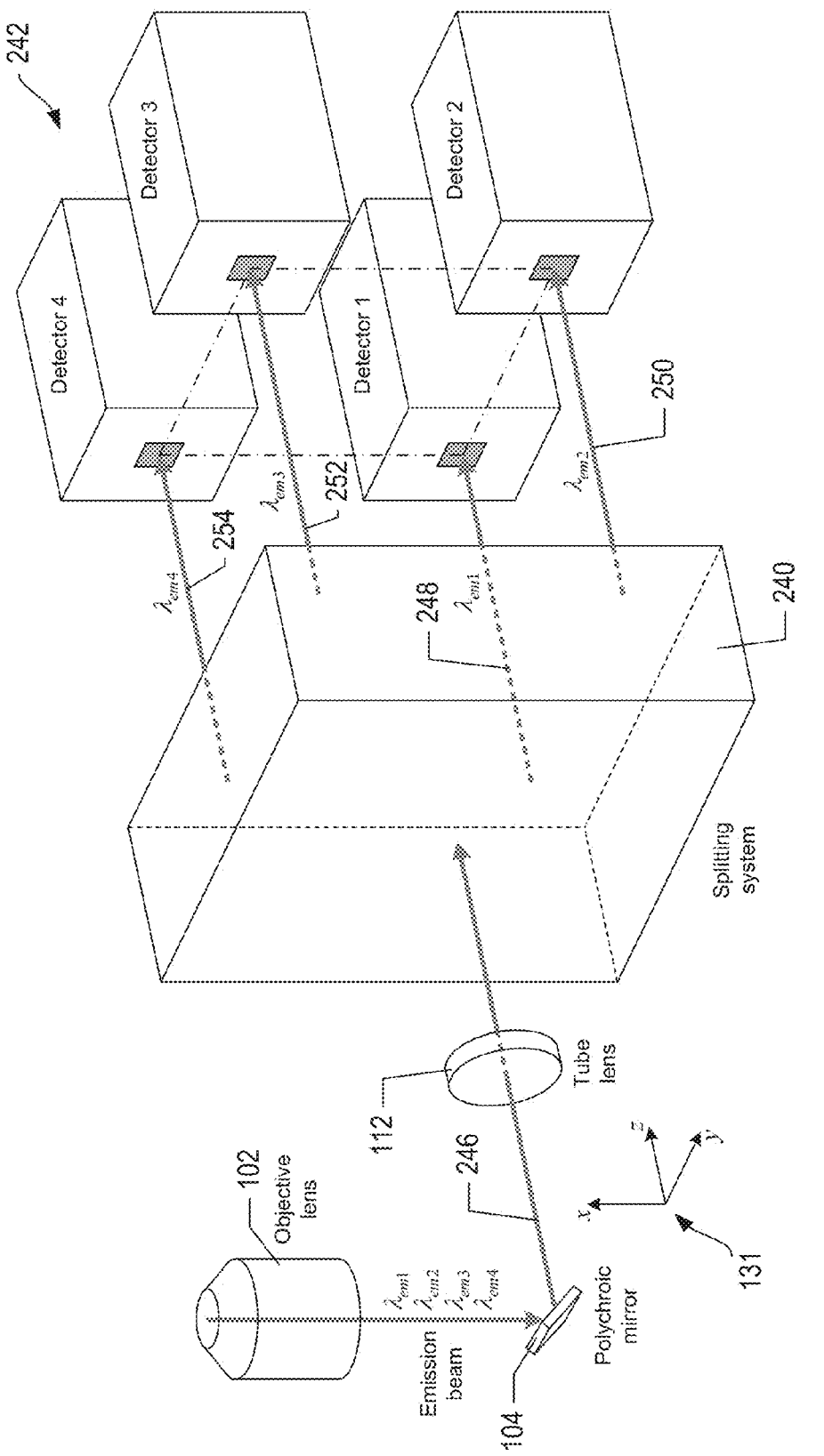

FIGS. 2A-2D show four examples of detection systems that each represent a different planar arrangement of the detectors. Each figure includes the objective lens 102, the polychroic mirror 104, and the tube lens 112 described above. In the example of FIG. 2A, the detection system includes a splitting system 202 and an array of two detectors 204. The two detectors lie along a line 206 oriented parallel to the y-axis. The splitting system 202 receives an emission beam of light 208 composed of two emission channels $\lambda_{em1}$ and $\lambda_{em2}$ and separates the two channels so that channel $\lambda_{em1}$ is output in a beam 210 to the detector 1 and channel $\lambda_{em2}$ is output in a beam 212 to the detector 2. The beams 210 and 212 lie in the yz-plane and are substantially parallel to one another. In the example of FIG. 2B, the detection system includes a splitting system 214 and an array of three detectors 216. The three detectors lie in the yz-plane. The splitting system 214 receives an emission beam of light 220 composed of three emission channels $\lambda_{em1}$, $\lambda_{em2}$ and $\lambda_{em3}$ and separates the channels so that channel $\lambda_{em1}$ is output in a beam 222 to the detector 1, channel $\lambda_{em2}$ is output in a beam 224 to the detector 2, and channel $\lambda_{em3}$ is output in a beam 226 to the detector 3. The beams 222, 224, and 226 lie in the yz-plane and are substantially parallel to one another. Note that detector 2 is placed farther from the splitting system 214 than the detectors 1 and 3 in order for the optical path lengths traveled by the beams 222, 224, and 226 to be approximately the same. In other embodiments, the detectors can lie along a line oriented parallel to the xy-plane by including mirrors in the splitting system 214 that reflect the beam 224 internally in order to increase the optical path length of the beam 224 to approximately match the optical path length traveled by the beams 222 and 226. The detectors are not limited to being arranged along a line parallel to the y-direction, the linear arrays of detectors 204 and 216 can be arranged along any line that lies in the xy-plane. In other embodiments, the output beams and the detectors can have a two-dimensional geometrical arrangement as represented in FIGS. 2C and 2D. In the example of FIG. 2C, the detection system includes a splitting system 228 and an array of three detectors 230. The three detectors are arranged so that each detector is located at a vertex of a triangle 232 oriented parallel to the xy-plane. In this example, the splitting system 228 receives the emission beam of light 220 and separates the channels so that channel $\lambda_{em1}$ is output in a beam 234 to the detector 1, channel $\lambda_{em2}$ is output in a beam 236 to the detector 2, and channel $\lambda_{em3}$ is output in a beam 238 to the detector 3. The beams 234, 236, and 238 are substantially parallel to one another. In the example of FIG. 2D, the detection system includes a splitting system 240 and an array of four detectors 242 arranged so that each detector is located at a vertex of a rectangle 244 oriented parallel to the xy-plane. In this example, the splitting system 240 receives and separates an emission beam of light 246 composed of four channels so that channel $\lambda_{em1}$ is output in a beam 248 to the detector 1, channel $\lambda_{em2}$ is output in a beam 250 to the detector 2, channel $\lambda_{em3}$ is output in a beam 252 to the detector 3, and channel $\lambda_{em4}$ is output in a beam 254 to the detector 4. The beams 248, 250, 252, and 254 are substantially parallel to one another.

Detection systems are not intended to be limited to planar arrays of up to four detectors. In other embodiments, detection systems can have five or more detectors in a planar geometric arrangement. For example, five detectors can be arranged so that the detectors are located at the vertices of a pentagon and six detectors can be arranged so that the detectors are located at the vertices of a hexagon. In other embodiments, the detectors can have an irregular planar arrangement and are not intended to be limited to planar, regular, two-dimensional geometrical arrangement.

The planar arrangement of detectors on one side or to the back of a microscopy instrument as described above is compact, which minimizes the footprint of the instrument. With all of the detectors located on one side or to the back of the instrument, the instrument can be more rapidly and conveniently installed in a smaller area and all of the cables and coolant tubes used to operate the detectors protrude from one side of the instrument rather than the cables and coolant tubes protrude from a number of different sides of the instrument, which improves the aesthetics of the instrument.

Figure 3A:
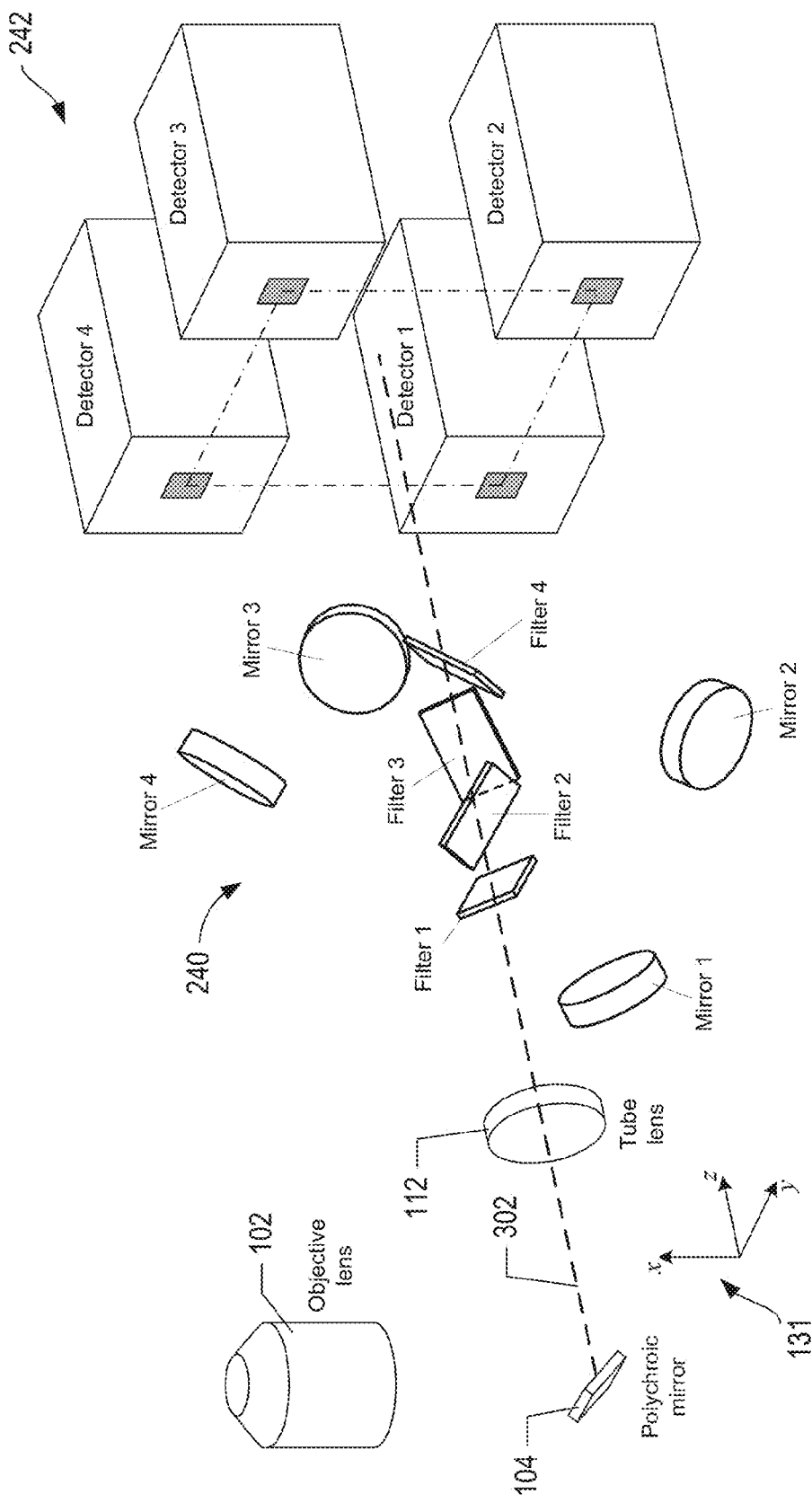
FIG. 3A shows an example implementation of a splitting system of the detection system shown in FIG. 2D.

Spitting systems can be implemented with a set of optical filters located along the emission axis of a microscopy instrument and a second set of mirrors positioned around the set of optical filters. Each filter is configured to reflect a particular channel to one of the mirrors while allowing transmission of other wavelengths. Each mirror is oriented to reflect one of the channels to a corresponding detector. The channels are reflected in substantially parallel output beams to the detectors as described above with reference to the examples shown in FIG. 2. FIG. 3A shows an example implementation of the splitting system 240 of the detection system shown in FIG. 2D. The splitting system 240 includes a set of four optical filters 1-4 arranged along an emission axis 302 that runs parallel to the z-axis and includes four mirrors 1-4 radially distributed around the set of filters.

Figure 3B:
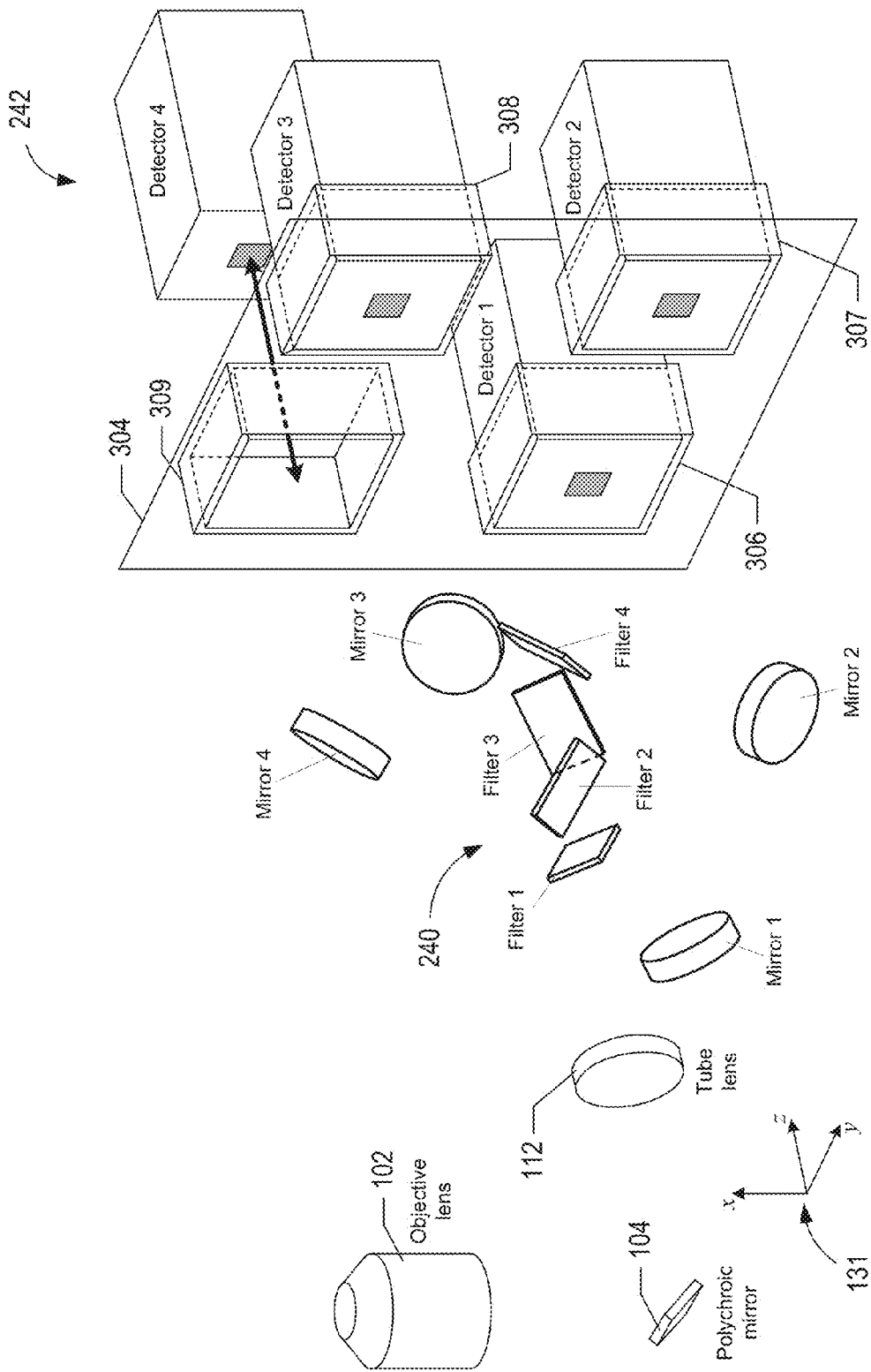
FIG. 3B shows an example of a schematic implementation of a back plate with four detector mounts.

In practice, the detectors of a detection system are attached to detector mounts in a back of a microscopy instrument and the detectors and the positions of the detectors may be varied slightly with respect to their distance from an ideal plane. FIG. 3B shows an example of a schematic implementation of a back plate 304 with four detector mounts 306-309. The mounts have rectangular planar arrangement in the xy-plane. As a result, when the detectors 1-4 are inserted into the corresponding mounts 306-309, the detectors 1-4 are substantially planar. The four separate mounts also allow the position of each of the detectors to be adjusted in the xy-plane and in the z-direction, in order to correct for refraction due to the beams passing through the filters, chromatic aberrations and other sources of optical path length variation.

The number of detectors of a microscopy system can be scaled up or down. In other words, a microscopy system that includes the detection system shown in FIG. 3B can be scaled down from a four detector detection system 242 to a three, two or a single detector detection system by removing any one, two or three detectors and the corresponding filters. Likewise, the detection system can be scaled up from a single, two or three detector detection system by placing detectors in the detector mounts and adding the corresponding filters to the splitting system. For example, in FIG. 3B, when the detector 4 is added to the mount 309, the corresponding filter 4 is added to the splitting system 240 and the detection system is scaled up from a three-detector system to a four-detector system. Alternatively, when the detector 4 is removed from the mount 309, the corresponding filter 4 is removed from the splitting system 240 and the detection system is scaled down from a four-detector system to a three-detector system.

Figure 4:
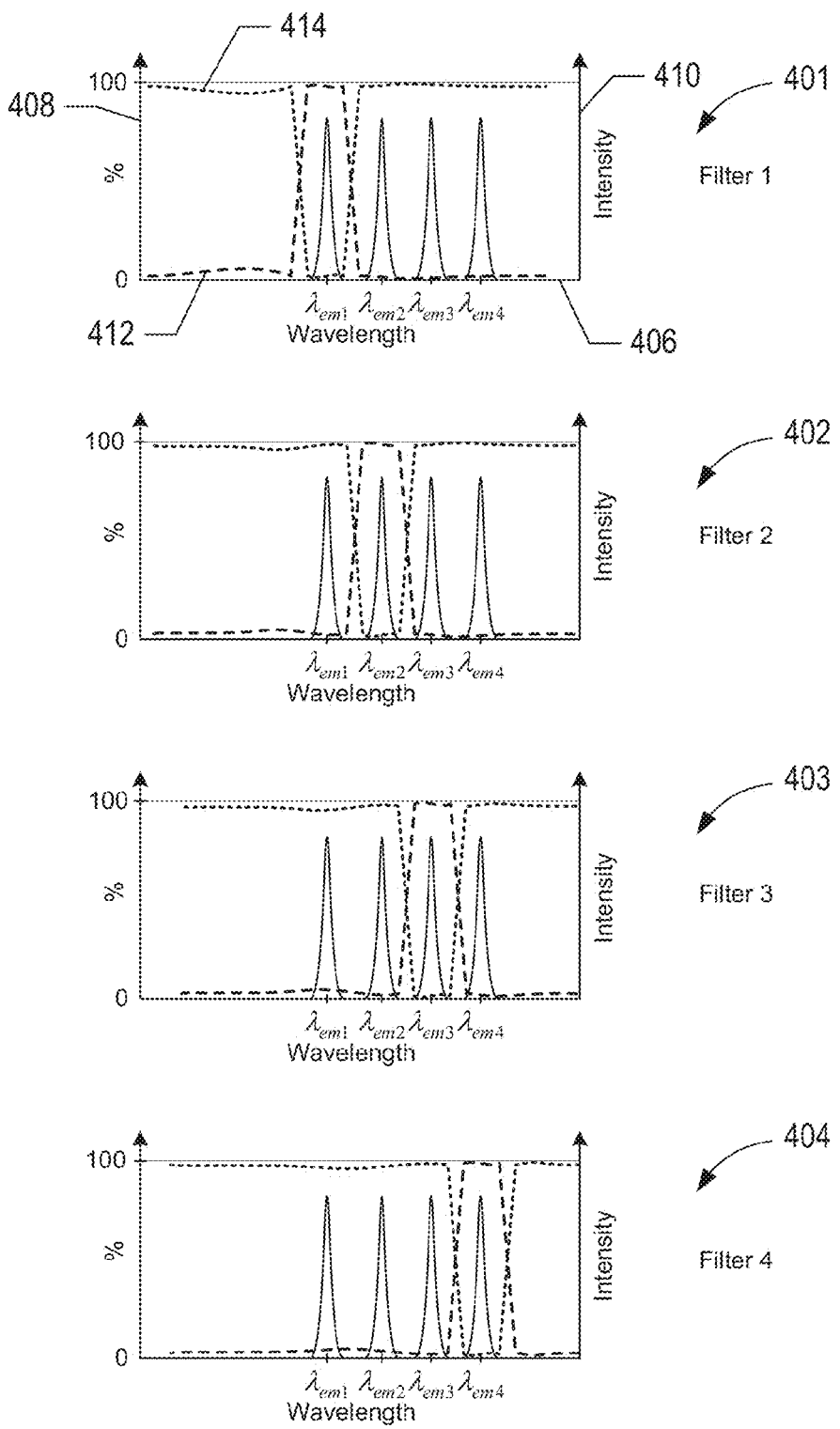
FIG. 4 shows example transmittance and reflectance plots associated with optical filters of a splitting system.

The filters 1-4 can be dichroic mirrors or polychroic mirrors. Each filter reflects one of the channels to a corresponding mirror. FIG. 4 shows example transmittance and reflectance plots 401-404 that represent the reflectance and transmittance properties associated with the filters 1-4, respectively. In each plot horizontal axes, such as axis 406, represent wavelength; vertical axes, such as axis 408, represent transmittance and reflectance as percentages; vertical axes, such as axis 410, represent channel intensity; dashed curves, such as dashed curve 412, represent reflectance; and dotted curves, such as dotted curve 414, represent transmittance. Each filter reflects one of the emission channels while transmitting other wavelengths. In particular, the example plots reveal that the filter 1 reflects the emission channel $\lambda_{em1}$, the filter 2 reflects the emission channel $\lambda_{em2}$, the filter 3 reflects the emission channel $\lambda_{em3}$, and the filter 4 reflects the emission channel $\lambda_{em4}$.

Figure 5:
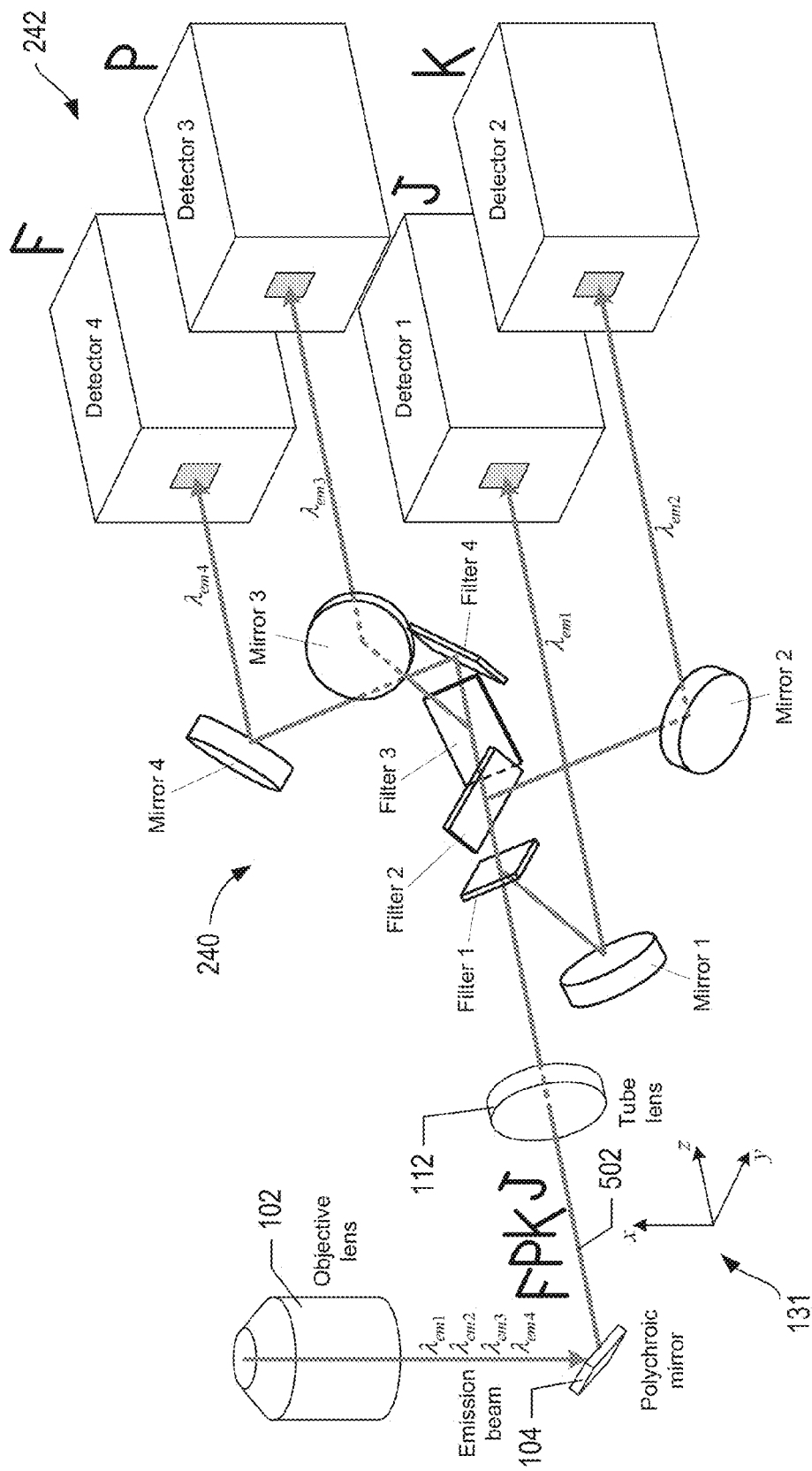
FIG. 5 shows an example of a splitting system in operation.

FIG. 5 shows the example splitting system 240 illustrated in FIG. 3 in operation with the filters configured to reflect and transmit light as described with reference to FIG. 4. An emission beam 502 composed of the four channels $\lambda_{em1}$, $\lambda_{em2}$, $\lambda_{em3}$, and $\lambda_{em4}$ is collected by the objective lens 102, reflected by the polychroic mirror 104 and collimated by the tube lens 112 before entering the splitting system 240. As the emission beam 502 passes through the splitting system 240, filter 1 reflects the channel $\lambda_{em1}$ toward mirror 1 and transmits channels $\lambda_{em2}$, $\lambda_{em3}$, and $\lambda_{em4}$; filter 2 reflects the channel $\lambda_{em2}$ toward mirror 2 and transmits channels $\lambda_{em3}$, and $\lambda_{em4}$; filter 3 reflects the channel $\lambda_{em3}$ toward mirror 3 and transmits channel $\lambda_4$; and filter 4 reflects the channel $\lambda_{em4}$ toward mirror 4. As shown in the example of FIG. 5, the mirrors 104 are radially distributed around the set of filters 104 and are oriented so that each channel is reflected in an output beam that is substantially parallel to the output beams associated with the other channels. In particular, as shown in FIG. 5, the mirrors 1-4 are oriented so that the respective channels $\lambda_{em1}$, $\lambda_{em2}$, $\lambda_{em3}$, and $\lambda_4$ are each reflected along separate, radially distributed, substantially parallel output beams to the detectors 1-4, respectively.

The optical elements of the splitting systems are arranged to preserve the orientations of the images associated with the channels. For example, when a specimen is illuminated with excitation light and each type of fluorescently labeled component emits light in a different emission channel, each type of component has an associated image in a color that corresponds to the emission channel wavelength. The splitting system separates the different images according to the emission channel wavelengths and each image is captured by one of the detectors. The optical elements of the splitting system do not reorient the separate images of the components. FIG. 5 also includes four letters "J," "K," "P," and "F" that are used to represent the orientations of images of four different types of components of a specimen that are fluorescently labeled to emit light in the emission channels $\lambda_{em1}$, $\lambda_{em2}$, $\lambda_{em3}$, and $\lambda_{em4}$, respectively. The splitting system 240 separates the images according to the associated emission channel wavelengths, but the orientation of each image is preserved as the image is twice reflected and finally transmitted to a corresponding detector. For example, the xy-plane orientations of the images associated with the letters "J," "K," "P," and "F" just before entering the splitting system 240 are the same as the orientations of the letters "J," "K," "P," and "F" in the xy-plane at the detectors 1-4. In other words, the images arrive at detectors 1-4 with the orientations of the images unchanged.

Figure 6:
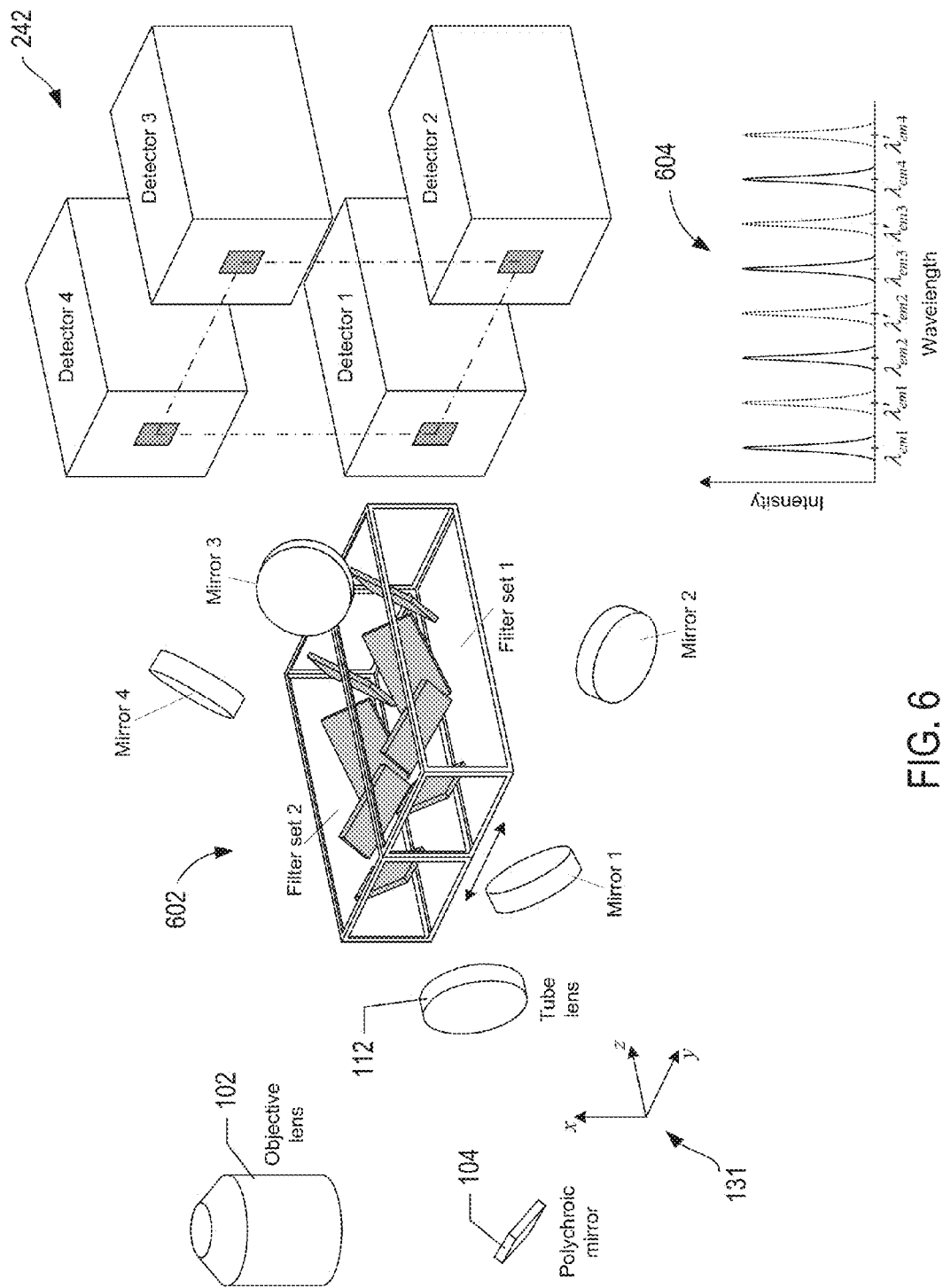
FIG. 6 shows an example of a splitting system with two interchangeable sets of optical filters.

In other embodiments, a spitting system can have more than one set of filters. Each set of filters reflects a different set of emission channels. FIG. 6 shows an example of a splitting system 602 with two sets of filters. In the example of FIG. 6, each set of filters is mounted within a chassis that enables the sets to be switched by sliding the sets back and forth in the y-direction. FIG. 6 includes an example plot 604 of two sets of emission channels associated with the filter sets 1 and 2. Filter set 1 is configured to reflect a first set of channels $\lambda_{em1}$, $\lambda_{em2}$, $\lambda_{em3}$, and $\lambda_{em4}$ represented by solid-line peaks, and filter set 2 is configured to reflect a second set of channels $\lambda'_{em1}$, $\lambda'_{em2}$, $\lambda'_{em3}$, and $\lambda'_{em4}$ represented by dashed-line peaks. When the filter set 1 is placed in the path of an emission beam composed of the two set of channels, the set 1 separates the first set of channels $\lambda_{em1}$, $\lambda_{em2}$, $\lambda_{em3}$, and $\lambda_{em4}$ in the manner described above with reference to FIG. 5. When the filter set 2 is placed in the path of the emission beam, the set 2 separates the second set of channels $\lambda'_{em1}$, $\lambda'_{em2}$, $\lambda'_{em3}$, and $\lambda'_{em4}$ in the manner described above.

The foregoing description, for purposes of explanation, used specific nomenclature to provide a thorough understanding of the disclosure. However, it will be apparent to one skilled in the art that the specific details are not required in order to practice the systems and methods described herein. The foregoing descriptions of specific examples are presented for purposes of illustration and description. They are not intended to be exhaustive of or to limit this disclosure to the precise forms described. For example, with reference to FIG. 1, the locations of the excitation filter 106 and the light source 108 can be switched with the locations of the emission filter 110, tube lens 112, splitting system 114 and the planar array of detectors 116 and the polychroic mirror 104 can be replaced with a polychroic mirror that reflects the excitation beam 118 to the objective lens 102 and transmits the emission beam 130. Obviously, many modifications and variations are possible in view of the above teachings. The examples are shown and described in order to best explain the principles of this disclosure and practical applications, to thereby enable others skilled in the art to best utilize this disclosure and various examples with various modifications as are suited to the particular use contemplated. It is intended that the scope of this disclosure be defined by the following claims and their equivalents:

The invention claimed is:
1. A fluorescence microscopy system comprising:
 a fluorescence microscopy instrument for imaging a specimen, the instrument comprising:

a splitting system to receive a beam composed of one or more channels of light, separate the channels, and direct the channels into separate, substantially parallel paths;

an array of detector mounts; and one or more detectors, wherein each detector is disposed within one of the detector mounts to receive one of the channels and the channels travel approximately equal optical path lengths, wherein the splitting system includes:

a set of mirrors; and one or more sets of optical filters, wherein each filter in each set is to reflect one of the channels toward one of the mirrors, and each mirror is positioned and oriented to reflect one of the channels into one of the separate, substantially parallel paths.

2. The fluorescence microscopy system of claim 1 further comprising a polychroic mirror to reflect the channels to the splitting system.

3. The fluorescence microscopy system of claim 1, wherein the set of the mirrors positioned around the set of filters further comprises the mirrors radially distributed around the set of optical filters.

4. The fluorescence microscopy system of claim 1, wherein the optical filters are dichroic mirrors.

5. The fluorescence microscopy system of claim 1, wherein the optical filters are polychroic mirrors.

6. The fluorescence microscopy system of claim 1, wherein the splitting system is to direct the channels into separate, substantially parallel paths further comprises the substantially, parallel paths lie in the same plane.

7. The fluorescence microscopy system of claim 1, wherein the splitting system is to direct the channels into separate, substantially parallel paths further comprises the substantially, parallel paths have a two-dimensional geometrical arrangement.

8. The fluorescence microscopy system of claim 1, wherein the array of detector mounts is approximately planar.

9. The fluorescence microscopy system of claim 1, wherein each detector further comprises one of a photodetector array, a CCD camera, or a CMOS camera.

10. A fluorescence microscopy system comprising:

a fluorescence microscopy instrument for capturing separate images of components of a specimen, the instrument comprising:

a light source to illuminate the specimen with an excitation beam of light that excites fluorescently labeled components to emit light in a number of different emission channels, each emission channel associated with particular component;

an objective lens to capture and direct the emission channels into an emission beam;

a splitting system to receive the emission beam, separate the beam into the emission channels, and direct the emission channels into separate, substantially parallel paths;

an array of detector mounts disposed on one side of the instrument; and one or more detectors, wherein each detector is disposed within one of the detector mounts to receive one of the channels and the channels travel approximately equal optical path lengths, wherein the splitting system includes:

a set of mirrors; and one or more sets of optical filters, wherein each filter in each set is to reflect one of the emission channels toward one of the mirrors, and each mirror is positioned and oriented to reflect one of the emission channels into one of the separate, substantially parallel paths.

11. The fluorescence microscopy system of claim 10 further comprising a polychroic mirror to reflect the emission channels to the splitting system.

12. The fluorescence microscopy system of claim 11, wherein the set of the mirrors positioned around the set of filters further comprises the mirrors radially distributed around the set of optical filters.

13. The fluorescence microscopy system of claim 11, wherein the optical filters are dichroic mirrors.

14. The fluorescence microscopy system of claim 11, wherein the optical filters are polychroic mirrors.

15. The fluorescence microscopy system of claim 11, wherein the splitting system is to direct the emission channels into separate, substantially parallel paths further comprises the substantially, parallel paths lie in the same plane.

16. The fluorescence microscopy system of claim 11, wherein the splitting system is to direct the emission channels into separate, substantially parallel paths further comprises the substantially, parallel paths have a two-dimensional geometrical arrangement.

17. The fluorescence microscopy system of claim 11, wherein each detector further comprises a photodetector array, a CCD camera, or a CMOS camera.

18. The fluorescence microscopy system of claim 11, wherein the splitting system preserves the orientation of the images associated with the components.

19. The fluorescence microscopy system of claim 11, wherein the array of detector mounts is approximately planar.

* * * * *